United States Patent [19]

Sugisawa et al.

[11] Patent Number: 4,687,739
[45] Date of Patent: Aug. 18, 1987

[54] METHOD FOR TREATING AQUEOUS SOLUTION OF SOYBEAN PROTEIN WITH ENZYMES

[75] Inventors: Ko Sugisawa; Masanori Yamamoto; Ataushi Yasuda; Yukihiro Nomura; Toshio Amano, all of Osaka, Japan

[73] Assignee: House Food Industries Co., Ltd., Osaka, Japan

[21] Appl. No.: 739,337

[22] Filed: May 30, 1985

[30] Foreign Application Priority Data

Jun. 8, 1984 [JP] Japan ................................ 59-116711

[51] Int. Cl.$^4$ .............................................. A23J 1/14
[52] U.S. Cl. ........................................ 435/69; 426/41; 426/46; 426/52; 426/565; 426/589; 426/656; 435/68; 435/272; 530/378
[58] Field of Search ....................... 260/112 R, 123.5; 426/41, 46, 52, 565, 589; 435/69, 68, 272; 530/378

[56] References Cited

U.S. PATENT DOCUMENTS

| | | | |
|---|---|---|---|
| 2,477,255 | 7/1949 | Keil et al. | 435/69 X |
| 3,694,221 | 9/1972 | Hoer et al. | 260/123.5 X |
| 3,761,353 | 9/1973 | Noe et al. | 435/272 X |
| 3,830,942 | 8/1974 | Hawley | 260/123.5 X |
| 3,852,480 | 12/1974 | Williams | 260/123.5 X |
| 3,857,966 | 12/1974 | Feldman et al. | 426/41 X |
| 3,876,806 | 4/1975 | Hempenius et al. | 426/46 |
| 3,889,001 | 6/1975 | Buide et al. | 426/565 |
| 3,897,570 | 7/1975 | Yokotsuka et al. | 426/52 X |
| 3,904,769 | 9/1975 | Sair et al. | 260/123.5 X |
| 4,105,799 | 8/1978 | Chandler et al. | 426/52 X |
| 4,107,334 | 8/1978 | Jolly | 426/52 X |
| 4,315,946 | 2/1982 | Greiner et al. | 426/52 X |
| 4,409,248 | 10/1983 | Lehnhard et al. | 260/123.5 X |
| 4,443,540 | 4/1984 | Chervan et al. | 435/69 |
| 4,477,472 | 10/1984 | Seto et al. | 426/46 |
| 4,632,903 | 12/1986 | Boyce et al. | 435/69 |

FOREIGN PATENT DOCUMENTS

| | | | |
|---|---|---|---|
| 51-73159 | 6/1976 | Japan | 426/589 |
| 0115838 | 10/1978 | Japan | 426/589 |
| 0190372 | 11/1983 | Japan | 426/589 |

Primary Examiner—Howard E. Schain
Attorney, Agent, or Firm—Armstrong, Nikaido, Marmelstein & Kubovcik

[57] ABSTRACT

There is provided a method for treating an aqueous solution of soybean protein to provide a calcium abundant bean soup drink. The method comprises the steps of adding endpeptidase to an aqueous solution of soybean protein the protein of which has been thermally or alkali denatured, causing the components of the mixture to react with each other under intense agitation, adding calcium salt to the reaction product and optionally adding oil and emulsifying agents to the resulting mixture and homogenizing the mixture.

7 Claims, No Drawings

METHOD FOR TREATING AQUEOUS SOLUTION OF SOYBEAN PROTEIN WITH ENZYMES

BACKGROUND OF THE INVENTION

This invention relates to a method for treating aqueous solutions of calcium abundant soybean protein and more particularly, to a method for treating aqueous solutions of calcium abundant soybean protein so as to prevent the precipitation of the soybean protein in the solution due to the addition of calcium to the solution to thereby preserve a high calcium concentration in the soybean protein.

Aqueous solutions of soybean protein represented by bean soup have been the object of attention as a drink containing excellent vegetable protein in an abundant amount in the art. However, aqueous solutions of soybean protein generally contain calcium in a less amount than milk and the insufficient calcium concentration is a nutritive disadvantage of the aqueous solutions of soybean protein.

In order to make up for the deficiency of calcium in the bean soup, when the bean soup is added thereto calcium salt in an amount sufficient to increase the calcium concentration in the bean soup to the same calcium concentration as that in milk, the problem that about 80 percent of the protein in the bean soup tends to precipitates in the soup arises.

The inventors have conducted researches in the solution of the problem and as a result of the researches, the inventors have found that the precipitation of protein in aqueous solutions of soybean protein due to the addition of calcium salt to the solution can be prevented by subjecting the aqueous solution of soybean protein to heat treatment or alkali treatment so as to denature the soybean protein in the aqueous solution of soybean protein and then adding endpeptidase to the thus pre-treated aqueous solution of soybean protein.

SUMMARY OF THE INVENTION

The present invention has been developed based on the above-mentioned finding and the present invention provides a method for treating aqueous solutions of soybean protein which essentially comprises the steps of adding endpeptidase to the aqueous solutions of soybean protein, the soybean protein in said aqueous solution having been thermally or alkali denatured, of causing the components of the thus obtained mixture to react with each other at a temperature in the range of 25°–95° C. for a time period in the range of 120 minutes – 1 minute under agitation and of adding calcium salt to the resulting reaction product. If desired or necessary, after the addition of calcium salt to the reaction product, the resulting mixture is subjected to homogenization treatment by adding oil and an emulsifying agent thereto and then processed in a suitable manner.

PREFERRED EMBODIMENT OF THE INVENTION

According to the present invention, first of all, an aqueous solution of soybean protein which has been previously subjected to a treatment by which the soybean protein in the solution is thermally or alkali denatured is provided. The aqueous solution of soybean protein is prepared by any one of the following three typical methods: (1) soybean which has been immersed in water or not immersed is triturated and then subjected to a centrifugal separation step to separate the bean cake from the soybean proper, (2) soybean is finely ground and then added water thereto to provide an aqueous solution of soybean protein and (3) isolated soybean protein powder from which the bean cake has been separated is added water thereto to provide an aqueous solution of soybean protein. The thus obtained aqueous solution of soybean protein preferably has a protein concentration in the range of 1–4% by weight based on the total weight of the solution.

In the method according to the present invention, before the aqueous solution of soybean protein is added endpeptidase thereto, it is necessary to subject the solution to a pre-treatment step in which the soybean protein in the aqueous solution of soybean protein is thermally or alkali denatured. When the soybean protein in the aqueous solution of soybean protein is previously subjected to the thermal or alkali denaturation step, the soybean protein can be easily decomposed by the enzymatic action of endpeptidase to be added to the aqueous solution in the subsequent step. Thus, the thermal or alkali denaturation treatment can be selectively employed provided that the soybean protein can be easily decomposed by the enzymatic action of endpeptidase. More particularly, when the thermal denaturation treatment is employed, the thermally pre-treated or denatured aqueous solution of soybean protein is heated at a temperature in the range of 85°–140° C. for a time period in the range of 1 hour–5 seconds and preferably at 90° C. in a time period in the range of 2 minutes–1 hour or at 140° C. in a time period in the range of 10 seconds–2 minutes. Alternatively, after the steaming of soybean, the steamed soybean is added water thereto to provide an aqueous solution of soybean protein in the above-mentioned manner. In the latter case, the obtained aqueous solution of soybean protein may be further heat-treated within the scope of the present invention. When an aqueous solution of soybean protein is subjected to the alkali treatment, the alkali treated aqueous solution of soybean protein is treated with an alkali group such as sodium hydroxide or potassium hydroxide to adjust the pH of the aqueous solution to a value above pH 10 and preferably to the order of pH 10–11.

Next, the thermally or alkali denatured aqueous solution of soybean protein is added endpeptidase thereto, but prior to the addition of endpeptidase to the aqueous solution, it is preferable that the pH of the soybean protein aqueous solution is adjusted to a value in the vicinity of its neutral equilibrium and more particularly, to the order of pH 6–8. Endpeptidases to be added to the aqueous solution of soybean protein include vegetable source ones represented by Bromelain and Ficin and microorganism source ones represented by actinomycete such as *Streptomyces griceus,* mold such as *Aspergillus oryzae* and *Bacillus subutilis.* The amount of endpeptidase to be added to the aqueous solution of soybean protein is above 0.1% by weight based on the total weight of the solution and preferably 0.4–3% by weight based on the total weight of the solution. After the addition of endpeptidase to the aqueous solution of soybean protein, the components in the resulting mixture are caused to react with each other at 25°–95° C. for 120 minutes to 1 minute under intense agitation. If the temperature is below the lower limit of the temperature range, the reaction time exceeds the upper limit of the time range. On the other hand if the temperature is above the upper limit of the temperature range, the endpeptidase completely loses its activity. Thus, when endpeptidase is added to the aqueous solution of soybean protein in the above-mentioned amount range and the components in the resulting mixture are caused to react with each other in the above-mentioned temperature range for the above-mentioned time period, the precipitation of the soybean protein in the aqueous solution thereof due to the addition of endpeptidase thereto can be substantially prevented. Although the reason has not been fully understood, it is assumed that since the soybean protein in the aqueous solution of soybean protein is partially decomposed to peptide on the order of ten-twenty thousand molecular weight, the reactivity of the soybean protein with calcium is lost. It is very important that the reaction of soybean with enzyme is carried out while agitating the aqueous solution of soybean protein. If the reaction is carried out without agitation, the soybean and enzyme form a gel in the reaction which makes it impossible to attain the object of the present invention.

After the denaturation of the soybean protein in the manner mentioned above, the denatured soybean protein is added calcium salt thereto. The calcium salt is preferably added to the soybean protein under intense agitation. Calcium salts which can be employed in the present invention include calcium chloride, calcium lactate, calcium gluconate and calcium glycerophosphate. The calcium salt is added to the aqueous solution of soybean protein in such an amount that the aqueous solution of soybean protein contains the calcium in a concentration ranging from 10 to 50 mM which is substantially the same calcium concentration in milk.

The above-mentioned method provides a calcium abundant aqueous soybean protein solution. If necessary or desired, the thus obtained aqueous soybean protein solution may be added thereto oil, an emulsifying agent and suitable relishes to homogenize the aqueous solution of soybean protein. The homogenization treatment is quite effective to prevent the precipitation of the soybean protein in the aqueous solution which would otherwise occur as a result of storage of the protein solution for a prolonged time period.

The thus treated aqueous solution of soybean protein is ready for drinking as it is or further added various relishes thereto to be served as a drink. Alternatively, the aqueous solution of soybean protein is added thereto gelling agent to become a jelly form soybean protein product.

EXPERIMENT 1

Soybean is immersed in water the amount of which is 9 times that of the soybean for 24 hours, triturated in the water and subjected to centrifugal separation to obtain a bean soup. The bean soup contains the soybean protein in the concentration of 3% by weight based on the total weight of the bean soup. The bean soup is then subjected to one of the following different treatment steps: (A) The bean soup is added calcium salt thereto without enzymatic treatment, (B) Without pre-heating, the bean soup is added thereto Bromelain (SIGMA) which has been dissolved in water, the soybean protein and Bromelain are caused to react with each other at 35° C. for 1 hour while intense agitating and the aqueous solution of soybean protein having Bromelain added thereto is further added thereto calcium chloride to obtain a bean soup and (C) The aqueous solution of soybean protein is pre-heated at 95° C. for 15 minutes, added thereto Bromelain which has been dissolved in water, the soybean protein and Bromelain are caused to react with each other at 35° C. for 1 hour under agitation by the use of a turbine type agitator having 86 cm diameter agitation blades and rotating at the rate of 600 r.p.m. and the thus treated aqueous solution of soybean protein is then added thereto calcium chloride to obtain a bean soup. Each of the bean soups obtained by the above-mentioned three different methods was subjected to centrifugal separation at the rate of 3000 r.p.m. and the amount of soybean protein remaining in the supernatant liquid was determined by the Kjeldahl method. The results of the determinations are given in Table 1 below. The amount of calcium chloride added to the aqueous solution of soybean protein was 25 mM in each of (A), (B) and (C). The amount of enzyme used in (B) and (C) was 1.0% by weight based on the total weight of protein.

TABLE 1

| Sample | Protein Amount (%) |
|---|---|
| (A) | 16.5 |
| (B) | 47.7 |
| (C) | 76.4 |

The amount of protein shown in Table 1 represents the ratio of the protein amount dissolved in the supernatant liquid to the total amount of protein in the entire bean soup.

When (A), (B) and (C) in Table 1 are compared with each other, it is apparent that the enzymatic treatment substantially prevents the precipitation of the protein in the bean soup due to the addition of calcium chloride. When (B) and (C) are compared with other, it is apparent that in the enzymatic treatment, the pre-heating of bean soup is quite effective to prevent the precipitation of the protein in the bean soup due to the addition of calcium chloride thereto.

As mentioned hereinabove, according to the method of the present invention, even when calcium chloride is added to an aqueous solution of soybean protein, the precipitation of the soybean protein in the solution due to the addition of the calcium chloride can be effectively prevented. As a result, the nutritive disadvantage of bean soups that the soup contains calcium in a less amount than milk can be eliminated and thus, the present invention provides aqueous solutions of soybean protein having substantially the same nutritive value as that of milk.

The present invention will be now exemplified by several examples thereof which merely illustrate the invention, but not for limiting the scope of the same in any way.

EXAMPLE 1

30 g of soybean protein powder is added to 1 liter of water, agitated in the water to be dispersed therein and heated at 120° C. for 2 minutes to provide an aqueous solution of soybean protein. The solution is cooled to 50° C. and added thereto 0.3 g of Pronase (Kaken Seiyaku Co., Ltd.) which has been dissolved in 10 ml of water. The resulting mixture is passed through a homogenizer under the pressure of 150 kg/cm$^2$ for 15 minutes to cause the components of the mixture to react with each other. Thereafter, the mixture is heated at 100° C. for 30 seconds to deprive the enzyme of its activity and then added thereto 4.4 g of calcium lactate to be dissolved in the mixture. The resulting mixture is further added thereto 10 g of corn oil and 0.5 g of sugar ester and passed through the abovementioned homogenizer at 150 kg/cm² to be homogenized to thereby obtain a calcium abundant bean soup.

EXAMPLE 2

200 g of exoleated soybean is washed in water and steamed at 100° C. for 10 minutes. The steamed soybean is added thereto 1.2 liters of hot water at 85° C., 1 g of calcium carbonate and 1.2 g of sodium hydride. The mixture is then triturated and subjected to centrifugal separation to obtain 1 kg of a bean soup. The bean soup is heated at 100° C. for 30 seconds and then allowed to cool to 95° C. whereupon the bean soup is added thereto 1 g of Bromelain (SIGMA) which has been dissolved in 30 ml of water under intense agitation and left as it is for 1 minute. The thus treated bean soup is added thereto 2.2 g of calcium chloride to be dissolved therein and further added thereto 10 g of maltose and 1 g of common salt to be dissolved therein to thereby obtain a calcium abundant bean soup drink.

EXAMPLE 3

1 kg of calcium abundant bean soup obtained by the procedure of Example 2 is adjusted to pH 11 with sodium hydride and left as it is for 5 hours. Then, the bean soup is again adjusted to pH 7 with hydrochloric acid. Next, the bean soup is added 3 g of Protease "Amano" A (Amano Pharmaceutical Co., Ltd.) which has been dissolved in 30 ml of water under intense agitation, and the mixture was kept 35° C. for 30 minutes. The treated bean soup is added 2.2 g of calcium chloride to be dissolved to obtain bean soup drink.

EXAMPLE 4

1 kg of calcium abundant bean soup obtained by the procedure of Example 2 is mixed with 1 kg of an aqueous solution containing 200 g of sugar and 15 g of low methoxyl pectin to thereby obtain a gelled calcium abundant food.

EXAMPLE 5

1 kg of soybean protein drink obtained by the procedure of Example 1 is added to 1 kg of an aqueous solution having 40 g of gelatin and 200 g of sugar dissolved therein and maintained at 80° C. The soybean protein drink and aqueous solution are fully admixed and the resulting mixture is cooled to 5° C. to thereby obtain a jelly containing calcium abundant soybean protein.

Although several specific examples of the invention have been described herein, many changes and modifications will of course suggest themselves to those skilled in the art. These examples have been selected for this disclosure for the purpose of illustration purpose only. The present invention should therefore not be limited to the examples so selected, the true scope of the invention being defined only in the appended claims.

What is claimed is:

1. A method for treating an aqueous solution of denatured soybean protein comprising the steps of:
    (a) adding endpeptidase to an aqueous solution of denatured soybean protein having a soybean protein concentration in the range of 1-4% by weight and and adjusted pH in the range of 6-8 to provide a mixture,
    (b) causing the components of said mixture to react with each other at a temperature in the range of 25°-95° for a time period in the range of 120 minutes-1 minute,, and
    (c) adding calcium salt to the reaction product in such an amount that the resulting mixture has a calcium concentration in the range of 10-50 mM.

2. The method as set forth in claim 1, further including the step of adding oil and an emulsifying agent to said reaction product after the addition of said calcium salt to thereby homogenize the reaction product.

3. The method as set forth in claim 1, in which said soybean protein has been thermally denatured.

4. The method as set forth in claim 1, in which said soybean protein has been alkali denatured.

5. The method as set forth in claim 1, further including the step of processing said reaction product after the addition of said oil and emulsifying agent.

6. The method as set forth in claim 1, in which said endpeptidase is selected from vegetable and microorganism sources.

7. The method as set forth in claim 1, in which said calcium salt is a member selected from the group consisting of calcium chloride, calcium lactate, calcium gluconate and calcium glycerophosphate.

* * * * *